United States Patent [19]

Inoue et al.

[11] Patent Number: 5,688,949
[45] Date of Patent: Nov. 18, 1997

[54] PYRAZOLO[1,5-A]PYRIMIDINE DERIVATIVES AND ANTI-INFLAMMATORY AGENT CONTAINING THE SAME

[75] Inventors: Makoto Inoue; Kinji Hashimoto, both of Naruto; Toshiko Kuwahara, Itano-gun; Yukio Sugimoto, Naruto; Takuji Uesako, Itano-gun; Toshiaki Funato, Tokushima, all of Japan

[73] Assignee: Otsuka Pharmaceutical Factory, Inc., Tokushima-ken, Japan

[21] Appl. No.: 133,086

[22] PCT Filed: Aug. 6, 1991

[86] PCT No.: PCT/JP91/01043

§ 371 Date: Oct. 7, 1993

§ 102(e) Date: Oct. 7, 1993

[87] PCT Pub. No.: WO92/18504

PCT Pub. Date: Oct. 29, 1992

[30] Foreign Application Priority Data

Apr. 22, 1991 [JP] Japan ................... 3-090707

[51] Int. Cl.$^6$ ............ C07D 487/04; A61K 31/505
[52] U.S. Cl. ........................... 544/281; 544/250
[58] Field of Search .................... 544/250, 281

[56] References Cited

U.S. PATENT DOCUMENTS

3,925,385  12/1975  O'Brien et al. ............ 424/251

FOREIGN PATENT DOCUMENTS

| A30141317 | 5/1985 | European Pat. Off. . |
| 2330400 | 11/1976 | France . |
| 2257547 | 6/1973 | Germany . |
| 61-57587 | 3/1985 | Japan . |
| 60-100581 | 4/1985 | Japan . |
| 3-204877 | 9/1991 | Japan ................... 544/281 |

OTHER PUBLICATIONS

Takamizawa, Chem Abs 64, 5088c (1966).
Shionogi, Chem Abs 67, 108663r (1967).
Derwent Abstract for JP40–2679 (1965).
Derwent Abstract for JP40–2680 (1965).
Shionogi Chemical Abstracts, vol. 67, Jul. 17, 1967, No. 3, No. 11500x.
Shionogi Chemical Abstracts, vol. 66, Jan. 16, 1967, No. 3, No. 10952h and 10957z.
McKillop Chemical Abstracts, vol. 87, Dec. 19, 1977, No. 25, No. 201460v.
Novinson Journal of Medicinal Chemistry, vol. 20, No. 2, Feb. 1977, pp. 296–299.
Springer Journal of Medicinal Chemistry, vol. 25, No. 3, Mar. 1982, pp. 235–242.
Robins Journal of Heterocyclic Chemistry, vol. 22, No. 3, May 1985, pp. 601–634.
Fomum Journal of Heterocyclic Chemistry, vol. 21, No. 4, Jul. 1984, pp. 1125–1128.
Delettre Journal of Heterocyclic Chemistry, vol. 15, No. 1, Jan. 1978, pp. 185–192.
Alcalde Journal of Heterocyclic Chemistry, vol. 11, No. 3, Jul. 1974, pp. 423–429.
Saito Bulletin of the Chemical Society of Japan, vol. 47, No. 2, Feb. 1974, pp. 476–480.
Database WPI, Week 9142, 91–306726 & Derwent Abstract for JP–A–3 204 877, Sep. 1991.
Shionogi Chemical Abstracts, vol. 67, Dec. 4, 1967, No. 23, No. 108663r.
Shionogi Chemical Abstract, vol. 67, Nov. 6, 1967, No. 19, No. 90832h.

*Primary Examiner*—Mark L. Berch
*Attorney, Agent, or Firm*—Sughrue, Mion, Zinn, Macpeak & Seas

[57] ABSTRACT

Pyrazolo[1,5-a]pyrimidine derivatives of the formula:

wherein $R_1$, $R_2$, $R_3$ and $R_4$ are H, carboxyl, lower alkoxycarbonyl, phenyl, lower alkyl optionally having a substituent selected from OH, carboxyl and lower alkoxy-carbonyl, or cycloalkyl, or $R_1$ and $R_2$ may combine each other to form lower alkylene; $R_5$ is group of —$SR_6$ or group of —$NR_7R_8$ in which $R_6$ is pyridyl or phenyl optionally having 1 to 3 substituents selected from OH and lower alkyl; and $R_7$ and $R_8$ are H, phenyl optionally having 1 to 3 substituents selected from OH, lower alkyl, lower alkoxycarbonyl and carboxyl, or $R_7$ and $R_8$ may combine each other to form with a nitrogen atom with which they bond 1-pyrrolidinyl, 2-oxo-1-pyrrolidinyl, or 1-piperazinyl group substituted by a phenyl group optionally being substituted by halogen or trihalomethyl, hydroxy-lower alkyl or diphenyl-lower alkyl, or a salt thereof, and anti-inflammatory agent containing as active ingredient compound of the above formula, wherein $R_1$, $R_3$ and $R_4$ are H, $R_2$ is lower alkyl or cycloalkyl, $R_5$ is group of —$NR_7R_8$ ($R_7$ is H, $R_8$ is phenyl substituted by OH and two lower alkyl).

3 Claims, No Drawings

PYRAZOLO[1,5-A]PYRIMIDINE DERIVATIVES AND ANTI-INFLAMMATORY AGENT CONTAINING THE SAME

TECHNICAL FIELD

The present invention relates to novel pyrazolo-[1,5-a] pyrimidine derivatives which are useful as medicaments, and an anti-inflammatory agent containing the same as an active ingredient.

More particularly, the present invention relates to a pyrazolo[1,5-a]pyrimidine derivative of the formula:

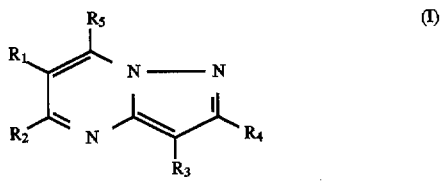

wherein $R_1$, $R_2$, $R_3$ and $R_4$ are the same or different and are each hydrogen atom, carboxyl group, a lower alkoxycarbonyl group, phenyl group, a lower alkyl group which may optionally be substituted by a group selected from hydroxyl group, carboxyl group and a lower alkoxycarbonyl group, or a cycloalkyl group, or $R_1$ and $R_2$ may combine each other to form a lower alkylene group; $R_5$ is a group of the formula: —$SR_6$ or a group of the formula: —$NR_7R_8$ in which $R_6$ is pyridyl group or a phenyl group which may optionally be substituted by 1 to 3 groups selected from hydroxyl group and a lower alkyl group; and $R_7$ and $R_8$ are hydrogen atom, a phenyl group which may optionally be substituted by 1 to 3 groups selected from hydroxyl group, a lower alkyl group, a lower alkoxycarbonyl group and carboxyl group, or $R_7$ and $R_8$ may combine each other to form with a nitrogen atom with which they bond 1-pyrrolidinyl group, 2-oxo-1-pyrrolidinyl group, or 1-piperazinyl group substituted by a phenyl group optionally being substituted by a halogen atom or a trihalomethyl group, a hydroxy-lower alkyl group or a diphenyl-lower alkyl group, or a salt thereof. Moreover, the present invention relates to an anti-inflammatory agent which contains as an active ingredient at least a compound of the pyrazolo[1,5-a]pyrimidine derivatives represented by the formula:

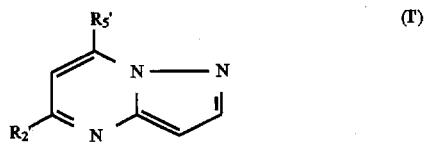

wherein $R_2'$ is a lower alkyl group or a cycloalkyl group, $R_5'$ is a group of the formula:

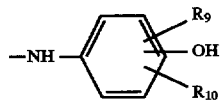

in which $R_9$ and $R_{10}$ are each a lower alkyl group, or a salt thereof.

BACKGROUND ART

Recently, it has been found that an arachidonic acid metabolite anticipates in inflammation. That is, arachidonic acid, which is one of the components comprising phospholipid existing on the cell membrane, may be released from the cell membrane by various stimulus, e.g. phlogogenic stimulus, antigen-antibody reaction (i.e. immunostimulation), etc., and then firstly metabolized by lipoxygenase or cyclooxygenase, etc., to be converted into various products. It has been proved that prostaglandin $E_2$ ($PGE_2$) and prostaglandin $I_2$ ($PGI_2$) which are produced by cyclooxygenase, or hydroxyperoxyeicosatetraenoic acids (HPETE) and hydroxyeicosatetraenoic acids (HETE) which are produced by lipoxygenase, anticipate in the above inflammation.

On the other hand, there have been known some anti-inflammatory agents which exhibit their anti-inflammatory activity by specifically inhibiting the above mentioned cyclooxygenase, such as indomethacin, ibuprofen, and the like. However, these agents have some problems, for instance, they cannot easily permeate into the affected parts, and hence, it has been expected to develop new agents which exhibit a potent anti-inflammatory activity especially in the form of external medicine preparations.

The present inventors have found that the pyrazolo[1,5-a]pyrimidine derivatives having the above formula (I) and their salts show various pharmacological actions, that particularly the compounds having the above formula (I') show excellent enzyme inhibitory activities and potent anti-inflammatory activities based thereon, and have achieved the present invention.

An object of the present invention is to provide novel pyrazolo[1,5-a]pyrimidine derivatives of the above formula (I) which are useful as a medicament. Another object of the present invention is to provide an anti-inflammatory agent containing as an active ingredient the compound of the above formula (I'). The other objects and advantages of the present invention are apparent to any skilled person in the art from the following description.

DISCLOSURE OF THE INVENTION

The novel pyrazolo[1,5-a]pyrimidine derivatives of the present invention have the above formula (I), and show various pharmacological activities, for example, ischemic-reperfusion disorder improving activity, anti-inflammatory activity, antirheumatic activity, activity for treatment of asthma, antiallergic activity, antipyretic and analgesic activity, etc., and hence, they are useful as a medicament such as drug for improving of ischemic-reperfusion disorder, anti-inflammatory agent, antirheumatic agent, drug for asthma, antiallergic agent, antipyretic analgesic, and the like, in animals, especially mammals. Moreover, the compound of the formula (I') is useful as anti-inflammatory agent based on excellent anti-inflammatory activity thereof.

Suitable examples of the groups in the above formulae (I) and (I') are as follows.

The "lower alkyl group" includes, for example, straight chain or branched chain alkyl groups having 1 to 6 carbon atoms such as methyl, ethyl, propyl, isopropyl, butyl, isobutyl, t-butyl, pentyl, hexyl, and the like.

The "lower alkoxycarbonyl group" includes, for example, straight chain or branched chain alkoxycarbonyl groups having 2 to 7 carbon atoms such as methoxycarbonyl, ethoxycarbonyl, propoxycarbonyl, isopropoxycarbonyl, butoxycarbonyl, t-butoxycarbonyl, pentyloxycarbonyl, hexyloxycarbonyl, and the like.

The "lower alkyl group which may optionally be substituted by a group selected from hydroxyl group, carboxyl group and a lower alkoxycarbonyl group" includes, for example, in addition to the above mentioned lower alkyl groups, hydroxymethyl, 2-hydroxyethyl, 3-hydroxypropyl, 2-hydroxypropyl, 2-hydroxyisopropyl, carboxymethyl, 2-carboxyethyl, 3-carboxypropyl, 4-carboxybutyl, methoxycarbonylmethyl, ethoxycarbonylmethyl, propoxycarbonylmethyl, butoxycarbonylmethyl, 2-methoxycarbonylethyl, 2-ethoxycarbonylethyl, and the like.

The "cycloalkyl group" includes, for example, cycloalkyl groups having 3 to 8 carbon atoms such as cyclopropyl, cyclobutyl, cyclopentyl, cyclohexyl, cycloheptyl, cyclooctyl, and the like.

The "lower alkylene group" includes, for example, methylene, ethylene, trimethylene, tetramethylene, pentamethylene, hexamethylene, and the like.

The "phenyl group which may optionally be substituted by 1 to 3 groups selected from hydroxyl group, a lower alkyl group, a lower alkoxycarbonyl group and carboxyl group" includes, for example, in addition to phenyl, 2-hydroxyphenyl, 3-hydroxyphenyl, 4-hydroxyphenyl, 2,3-dihydroxyphenyl, 2,4-dihydroxyphenyl, 3,4-dihydroxyphenyl, 2-methylphenyl, 1,3-dimethylphenyl, -3,4,5-trimethylphenyl, 3-ethylphenyl, 2,3-diethylphenyl, 2,4,6-triethylphenyl, 4-propylphenyl, 2,4-dipropylphenyl, 1,2,3-tripropylphenyl, 4-t-butylphenyl, 2,4-di-t-butylphenyl, 2,4,6-tri-t-butylphenyl, 3,5-di-t-butyl-4-hydroxyphenyl, 2-methoxycarbonylphenyl, 3-methoxycarbonyl-4-hydroxyphenyl, 2-carboxyphenyl, 3-carboxyphenyl, 4-carboxyphenyl, 2,4-dicarboxyphenyl, 2,4,6-tricarboxyphenyl, 3-carboxy-4-hydroxyphenyl, and the like.

The "phenyl group optionally being substituted by a halogen atom or a trihalomethyl group" includes, for example, in addition to phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-fluoro-3-chlorophenyl, 2-trifluoromethylphenyl, 3-trichloromethylphenyl, 4-tribromomethylphenyl, 2-triiodomethylphenyl, 3-difluoromonochloromethylphenyl, 4-monochlorodibromomethylphenyl, 2-dichloromonoiodomethylphenyl, and the like.

The "diphenyl-lower alkyl group" includes, for example diphenylmethyl, 2,2-diphenylethyl, 2,3-diphenylpropyl, and the like.

The pyrazolo[1,5-a]pyrimidine derivatives of the present invention can be prepared by the following reaction schemes.

[Reaction Scheme-1]

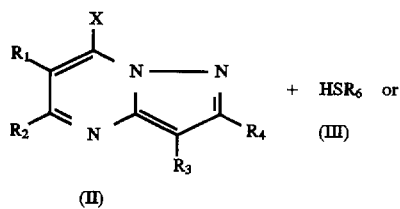

(II)

+ HSR$_6$ or (III)

-continued
[Reaction Scheme-1]

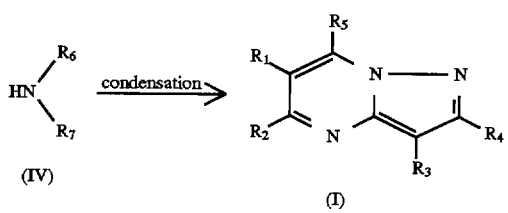

(IV)

(I)

wherein X is a halogen atom, and R$_1$, R$_2$, R$_3$, R$_4$, R$_5$, R$_6$, R$_7$ and R$_8$ are the same as defined above.

As shown in Reaction Scheme-1, the compounds (I) of the present invention can be prepared by the condensation reaction of a pyrazol[1,5-a]pyrimidine halide derivative (II) and a thiol compound (III) or an amine compound (IV).

The above reaction is usually carried out in a suitable solvent in the presence or absence of an acid acceptor. The acid acceptor includes, for example, inorganic bases such as hydroxides, hydrogen carbonates and carbonates of alkali metals (e.g. NaOH, KOH, NaHCO$_3$, K$_2$CO$_3$, etc.), or tertiary amines such as triethylamine, dimethylaniline, diethylaniline, N-methylmorpholine, pyridine, 4-dimethylaminopyridine, and the like. The solvent includes, for example, inert organic solvents such as lower alcohols (e.g. methanol, ethanol, etc.) and ethers (e.g. tetrahydrofuran,(THF), dioxane, etc.). When an inorganic base is used as an acid acceptor, it is preferable to use as a solvent a mixture of an inert organic solvent and water. Moreover, aromatic hydrocarbons (e.g. benzene, toluene, xylene, etc.) may also be used as a solvent.

In the above reaction, the ratio of the pyrazolo[1,5-a] pyridimidine halide derivative (II) and the thiol compound (III) or the amine compound (IV) is not specified, but the latter is used in an equimolar or excess amount to one mole of the former. The above acid acceptor is preferably used in an amount of equimolar or excess amount to one mole of the pyrazolo[1,5-a]pyrimidine halide derivative. The reaction is carried out either under cooling, at room temperature or under heating, but it is usually carried out at a temperature of 0° C. to a refluxing temperature of the solvent used therein, for 0.5 to 15 hours.

[Reaction Scheme-2]

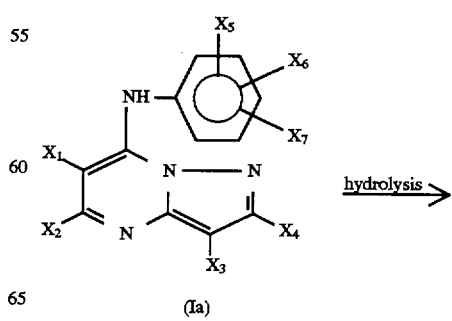

(Ia)

hydrolysis →

-continued
[Reaction Scheme-2]

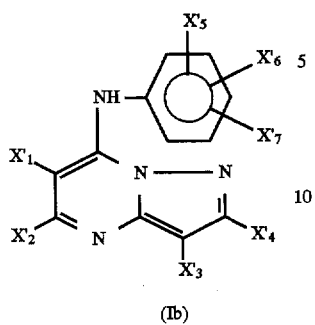

(Ib)

wherein $X_1$–$X_7$ and $X'_1$–$X'_7$ are each the corresponding group in the above formula (I), that is, $X_1$ and $X'_1$, $X_2$ and $X'_2$, $X_3$ and $X'_3$, $X_4$ and $X'_4$ correspond to $R_1$, $R_2$, $R_3$ and $R_4$, respectively, and $X_5$ and $X'_5$, $X_6$ and $X'_6$, $X_7$ and $X'_7$ are hydrogen atom, hydroxyl group, a lower alkyl group, a lower alkoxycarbonyl group or carboxy group, provided that at least one of $X_1$, $X_2$, $X_3$, $X_4$, $X_5$, $X_6$ and $X_7$ is a lower alkoxycarbonyl group or a lower alkoxycarbonyl-lower alkyl group, and a group in $X'_1$, $X'_2$, $X'_3$, $X'_4$, $X'_5$, $X'_6$, $X'_7$, of which position is the same as that of the above group, is carboxyl group or a carboxy-lower alkyl group.

As shown in Reaction Scheme-2, one of the compounds of the present invention (Ib) can be prepared by hydrolysis of the compound (Ia) which is one of the compounds (I) prepared in Reaction Scheme-1 and has a lower alkoxycarbonyl group and/or a lower alkoxycarbonyl-lower alkyl group as a substituent. The above reaction is carried out in a mixed solvent of water and an inert solvent such as lower alcohols (e.g. methanol, ethanol, etc.), ethers (e.g. THF dioxane, etc.) in the presence or absence of an alkali metal hydroxide (e.g. NaOH, KOH, etc.) and sodium hydrosulfate ($Na_2S_2O_4$) in an amount of 1 to 30 moles to one mole of the compound (Ia). When one of $X_5$, $X_6$ and $X_7$ is OH group positioning at p-position to the NH group, said OH group possibly be oxidazed during the hydrolysis, and hence, the reaction is preferably carried out in the presence of $Na_2S_2O_4$. The reaction may proceed either under cooling, at room temperature or under heating, but it is usually carried out at a temperature of 0° C. to a refluxing temperature of the solvent used.

[Reaction Scheme-3]

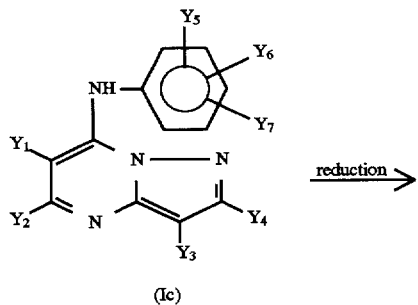

(Ic)

-continued
[Reaction Scheme-3]

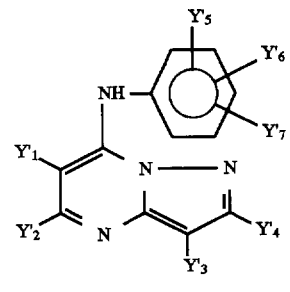

(Id)

wherein $Y_1$–$Y_7$ and $Y'_1$–$Y'_7$ are each the corresponding group in the formula (I), that is, $Y_1$ and $Y'_1$, $Y_2$ and $Y'_2$, $Y_3$ and $Y'_3$, and $Y_4$ and $Y'_4$ are $R_1$, $R_2$, $R_3$ and $R_4$, respectively, $Y_5$ and $Y'_5$, $Y_6$ and $Y'_6$, $Y_7$ are hydrogen atom, hydroxyl group, a lower alkyl group, a lower alkoxycarbonyl group or carboxy group, provided that at least one of $Y_1$, $Y_2$, $Y_3$, $Y_4$, $Y_5$, $Y_6$, $Y_7$ is carboxyl group, a lower alkoxycarbonyl group or a carboxy-lower alkyl group, and a group in $Y'_1$, $Y'_2$, $Y'_3$, $Y'_4$, $Y'_5$, $Y'_6$ and $Y'_7$, of which position is the same as the said group, is hydroxyl group or a hydroxy-lower alkyl group.

As shown in Reaction Scheme-3, one of the compounds of the present invention (Id) can be prepared by the reduction of the compound (Ic), which is one of the compounds (I) prepared in Reaction Scheme-1 and has a carboxyl group, a lower alkylcarbonyl group and/or a carboxy-lower alkyl group. The above reduction reaction is carried out in an inert organic solvent such as diethyl ether, THF, dioxane, etc., by using a suitable reducing agent such as lithium aluminum hydride, aluminum hydride, diborane, etc. in an amount of 1 to 10 moles to one mole of the compound (Ic). The reaction is carried out at a temperature of about 0° to 50° C., preferably at a temperature of about 0° C. to room temperature.

In the above Reaction Scheme-1, the compound (II) used as a starting compound includes both a known compound and a novel compound, and these compounds may be prepared, for example, by a method disclosed in the following Reaction Scheme-4.

[Reaction Scheme-4]

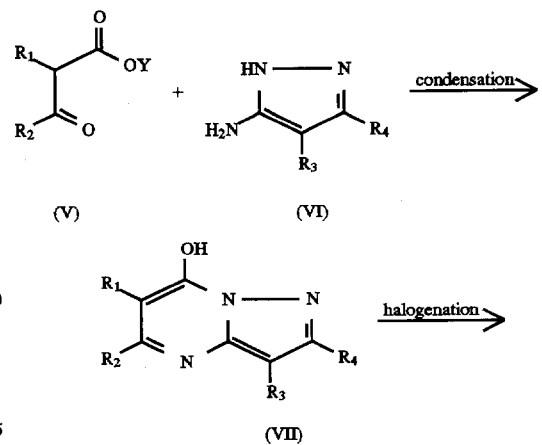

-continued
[Reaction Scheme-4]

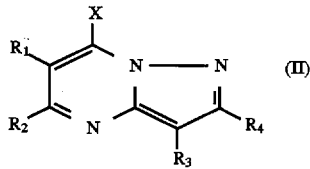

wherein Y is a lower alkyl group, and $R_1$, $R_2$, $R_3$, $R_4$ and X are the same as defined above.

The condensation reaction between the compound (V) and the compound (VI) in Reaction Scheme-4 is carried out in a solvent such as acetic acid, ethanol, etc., at a temperature of room temperature to a boiling point of the solvent.

The compound (V) is used in an amount of almost equimolar to the compound (VI), and the reaction is carried out for 2 to 5 hours to give the compound (VII).

Subsequently, the compound (II), the starting compound of the present invention, is prepared by halogenating the compound (VII).

The halogenation reaction is carried out by treating with a halogenating agent such as phosphorus oxychloride, phosphorus oxybromide, etc. in the presence of an acid acceptor such as N,N-dimethylaniline, N,N-diethylaniline, triethylamine, etc. Besides, the above halogenating agent may also be used as a solvent, and hence, the reaction does not need any solvent but can be carried out in another inert solvent such as benzene, toluene, xylene, etc.

Moreover, the acid acceptor is used in an amount of about 1 to 10 moles to 1 mole of the compound (VII).

The reaction is carried out at a temperature of room temperature to 100° C., for 0.5 to two hours.

The compounds obtained in above Reaction Schemes 1 to 4 can be purified and isolated from the reaction system by a conventional separation method. The conventional method for isolating and purification is, for example, extraction with a solvent, distillation, recrystallization, column chromatography, preparative thin layer chromatography, and the like. The compounds of the present invention thus obtained may be isolated, if necessary, in the form of a free base, or in the form of an acid addition salt with a pharmaceutically acceptable acid such as inorganic acids (e.g. hydrochloric acid, hydrobromic acid, sulfuric acid, nitric acid, etc.) or organic acids (e.g. oxalic acid, fumaric acid, maleic acid, tartaric acid, citric acid, etc.), or in the form of a metal salt with a pharmaceutically acceptable alkali metals or alkaline earth metals (e.g. sodium, potassium, calcium, etc.).

The anti-inflammatory agent of the present invention is used in the form of a pharmaceutical preparation containing an effective amount of at least one if the above compounds (I') and salts thereof.

The pharmaceutical preparation form and the administration route of the present anti-inflammatory agent may be any conventional ones, but it is advantageous to administer the present anti-inflammatory agent locally in the form of an external preparation such as creams, ointments, lotions, aerosols, etc. These pharmaceutical preparations may be prepared by a conventional method with a conventional nontoxic pharmaceutical excipinent. The base for preparation of creams, ointments, etc. is, for example, white soft paraffine, paraffine, glycerin, bees wax, cellulose derivatives (e.g. methyl cellulose, etc.), glyceryl monostearate, cetostearyl alcohol, octyldodecanol, medium-chain fatty acid triglyceride, polyethyleneglycol, silicone, bentonite, and the like. In the liquid preparations (e.g. lotions, etc.) and aerosols, the solvent for dissolving an active ingredient includes, for example, water, ethyl alcohol, isopropyl alcohol, propyleneglycol, 1,3-butyleneglycol, polyethyleneglycol, crotamiton, and the like, and the surfactant includes, for example, sorbitan fatty acid esters, polyoxyethylenesorbitan fatty acid esters, polyoxyethylene fatty acid esters, polyoxyethylene ethers of hydrogenated castor oil, lecithin, self-emulsifiable-type glyceryl monostearate, and the like. Moreover, the preparation of the present invention may be prepared in the form of a suspension, and the suspending agent includes, for example, cellulose derivatives (e.g. carboxymethyl cellulose sodium salt, methyl cellulose, etc.), and natural gums (e.g. tragacanth, gum arabic, etc.), and the like.

The present preparations thus prepared may contain a conventional preservative (e.g. p-hydroxybenzoic acid ester, benzalkonium chloride, sorbitan acid salt, etc.), or other various additives, if necessary.

The clinical dosage of the present anti-inflammatory agent varies depending on ages, weights, sensibility of the patients, and severities of the diseases, but it is usually in the range of about 0.001 to 10 g, preferably about 0.02 to 5 g per day for an adult. The dosage may, of course, be out of this range depending on the conditions of the patients.

BEST MODE FOR CARRYING OUT THE INVENTION

The present invention is illustrated in more detail by the following Examples wherein the present compounds are prepared, Preparations and Pharmacological experiments.

EXAMPLE 1

Preparation of 7-(3,5-di-t-butyl-4-hydroxyphenyl)-aminopyrazolo[1,5-a]pyrimidine:

A suspension of 7-chloropyrazolo[1,5-a]pyrimidine (1.0 g), 3,5-di-t-butyl-4-hydroxyaniline hydrochloride (1.8 g) and diethylaniline (2.3 ml) in toluene (50 ml) is heated at 120° C. for 30 minutes. After cooling, the solvent is distilled off, and the residue is purified by silica gel column chromatography (solvent; $CHCl_3$) to give 7-(3,5-di-t-butyl-4-hydroxyphenyl)aminopyrazolo[1,5-a]pyrimidine (890 mg) as colorless crystal.

M.p. 264°–266° C. (decomposed)

$^1$H-NMR ($CDCl_3$): δ

1.48 (s, 18H), 5.63 (s, 1H), 5.92 (s, 1H), 6.55 (d, J=2.3 Hz, 1H), 7.47 (s, 2H), 8.14 (d, J=2.3 Hz, 1H)

EXAMPLE 2

Preparation of 5-methyl-7-(3,5-di-t-butyl-4-hydroxyphenyl)aminopyrazolo[1,5-a]pyrimidine:

A suspension of 5-methyl-7-chlorohyrazolo[1,5-a]-pyrimidine (3.5 g) and 3,5-di-t-butyl-4-hydroxyaniline hydrochloride (6.0 g) and diethylaniline (6.0 g) in toluene (150 ml) is heated at 120° C. for 30 minutes, and cooled. The reaction mixture is poured into water, and extracted with dichloromethane. The organic layer is dried over anhydrous magnesium sulfate and concentrated. The residue is purified by silica gel column chromatography (solvent; dichloromethane/ethyl acetate/methanol=5:1:1) to give the title compound (4.7 g) as colorless crystal.

M.p. 251°–253° C.

1H-NMR (DMSO-$d_6$, internal standard: TMS): δ

1.41 (s, 18H), 2.35 (s, 3H), 6.05 (s, 1H), 6.35 (d, J=2.0 Hz, 1H), 7.18 (s, 2H), 8.09 (d, J=2.0 Hz, 1H), 9.5 (brs, 1H)

EXAMPLES 3 TO 26

The compounds listed in the following Table 1 are obtained in the same manner as in Example 1.

TABLE 1

[Structure: pyrazine-pyrazole fused core with substituents $R_1$, $R_2$, $R_3$, $R_4$, $R_5$]

| Ex. No. | $R_1$ | $R_2$ | $R_3$ | $R_4$ | $R_5$ | M.p. °C. | $^1$H-NMR δ value (internal standard: TMS) |
|---|---|---|---|---|---|---|---|
| 3 | H | Me | H | H | —NH—(2-MeO₂C-phenyl) | 140–142 | CDCl₃: 2.56(s, 3H), 3.99(s, 3H), 6.50(d, J=2.3H, 1H), 6.62(s, 1H), 7.18(t-d, J=7.3, 1.0Hz, 1H), 7.64(t-d, J=7.3, 1.7Hz, 1H), 7.75 (d-d, J=7.3, 1.0Hz, 1H), 8.1–8.2(m, 2H) |
| 4 | H | Me | H | H | —NH—(4-OH-3-CO₂Me-phenyl) | 188–189 | CDCl₃: 2.46(s, 3H), 3.98(s, 3H), 5.93(s, 1H), 6.46(d, J=2.5Hz, 1H), 7.10(d, J=8.9Hz, 1H), 7.48(d-d, J=8.9, 2.7Hz, 1H), 7.85(d, J=2.7Hz, 1H), 7.86(brs, 1H), 8.01(d, J=2.5Hz, 1H), 10.82(s, 1H) |
| 5 | H | Me | H | Ph | —NH—(4-OH-3-CO₂Me-phenyl) | 245–246 (dec.) | CDCl₃—CD₃OD: 2.64(s, 3H), 3.99(s, 3H), 5.92(s, 1H), 7.07(s, 1H), 7.20(d, J=8.8Hz, 1H), 7.4–7.5(m, 3H), 7.56(d-d, J=8.8, 2.6 Hz, 1H), 7.95(d, J=2.6Hz, 1H), 8.0–8.1(m, 2H) |
| 6 | H | Me | H | Ph | —N(piperazinyl)—Ph | 197–199 | CDCl₃: 2.54(s, 3H,) 3.48(t, J=5.0Hz, 4H), 3.95(t, J=5.0Hz, 4H), 6.03(s, 1H), 6.77(s, 1H), 6.94(t, J=7.2Hz, 1H), 7.03(d, J=8.4Hz, 2H), 7.3–7.5(m, 5H), 8.00(d-d, J=7.2, 1.5Hz, 2H) |
| 7 | H | Me | H | Ph | —N(piperazinyl)—N—CH₂CH₂OH | 210–215 (dec.) | CDCl₃—CD₃OD: 2.52(s, 3H), 2.69(t, J=5.6Hz, 2H), 2.85(t, J=4.9Hz, 4H), 3.76(t, J=5.6Hz, 2H), 3.86(t, J=4.9Hz, 4H), 6.05(s, 1H), 6.74(s, 1H), 7.3–7.5(m, 3H), 7.98(d, J=6.9Hz, 2H) |
| 8 | H | Me | H | Ph | —N(pyrrolidinyl) | 194–196 | CDCl₃: 2.0–2.1(m, 4H), 2.43(s, 3H), 4.0–4.1(m, 4H), 5.59(s, 1H), 6.59(s, 1H), 7.3–7.5(m, 3H), 7.95(d-d, J=7.6, 1.7Hz, 2H) |
| 9 | H | Me | H | Ph | —NH—(3,5-di-t-Bu-4-OH-phenyl) | 280–282 (dec.) | CDCl₃: 1.47(s, 18H), 2.46(s, 3H), 5.32(s, 1H), 6.02(s, 1H), 6.72(s, 1H), 7.18(s, 2H), 7.3–7.5(m, 3H), 8.00(d, J=8.1Hz, 2H) |
| 10 | H | Me | CO₂Et | H | —NH—(3,5-di-t-Bu-4-OH-phenyl) | 213–215 | DMSO-d₆: 1.31(t, J=7.1Hz, 3H), 1.40(s, 18H), 2.49(s, 3H), 4.26 (q, J=7.1Hz, 2H), 6.22(s, 1H), 7.14(s, 1H), 7.16(s, 1H), 8.48(s, 1H), 9.83(s, 1H) |
| 11 | H | Me | CO₂Et | H | —N(piperazinyl)—N—CH₂CH₂OH | 208–210 (dec.) | CDCl₃: 1.41(t, J=7.1Hz, 3H), 2.63(s, 3H), 2.67(t, J=5.3Hz, 2H), 2.79(t, J=4.9Hz, 4H), 3.70(t, J=5.3Hz 2H), 3.77(t, J=4.9Hz, 4H), 4.40(q, J=7.1Hz, 2H), 6.14(s, 1H), 8.41(s, 1H) |

TABLE 1-continued

[Structure: pyrazolo-pyrimidine core with substituents R1, R2, R3, R4, R5]

| Ex. No. | R₁ | R₂ | R₃ | R₄ | R₅ | M.p. °C. | ¹H-NMR δ value (internal standard: TMS) |
|---|---|---|---|---|---|---|---|
| 12 | H | Me | CO₂Et | H | —NH—[phenyl with OH·HCl and CO₂Me] | 170–173 | DMSO-d₆: 1.35(t, J=7.2Hz, 3H), 2.55(s, 3H), 3.90(s, 3H), 4.36(q, J=7.2Hz, 2H), 6.37(s, 1H), 7.20(d, J=8.9Hz, 1H), 7.58(d-d, J=8.9, 2.5Hz, 1H), 7.81(d, J=2.5Hz, 1H), 8.69(s, 1H) |
| 13 | H | Me | Ph | H | —NH—[phenyl with two C₄H₉(t) and OH] | 222–224 | DMSO-d₆: 1.42(s, 18Hz), 2.44(s, 3H), 6.12(s, 1H), 7.10(s, 1H), 7.19(s, 2H), 7.17–7.22(m, 1H), 7.40(d-d, J=7.5, 7.5Hz, 2H), 8.19(d, J=7.5Hz, 2H), 8.63(s, 1H), 9.61(s, 1H) |
| 14 | H | Me | Ph | H | —NH—[phenyl with MeO₂C] | 174–175 | DMSO-d₆: 2.55(s, 3H), 3.89(s, 3H), 6.77(s, 1H), 7.24 d-d, J=8.0, 8.0Hz, 1H), 7.32(d-d, J=8.0, 8.0Hz, 1H), 7.45(d-d, J=8.0, 8.0Hz, 2H), 7.76(d-d, J=8.0, 8.0Hz, 1H), 7.89(d, J=8.0Hz, 1H), 8.06 (d, J=8.0Hz, 1H), 8.18(d, J=8.0Hz, 2H), 8.71(s, 1H), 11.00(s, 1H) |
| 15 | CO₂Et | H | H | H | —NH—[phenyl with two C₄H₉(t) and OH] | 248–250 (dec.) | DMSO-d₆: 0.90(t, J=7.2Hz, 3H), 1.35(s, 18Hz), 3.56(q, J=7.2Hz, 2H), 6.61(d, J=2.2Hz, 1H), 6.98 (s, 1H), 7.00(s, 2H), 7.23(d, J=2.2Hz, 1H), 8.42 (s, 1H), 10.26(s, 1H) |
| 16 | CH₂CO₂Et | Me | H | H | —NH—[phenyl with two C₄H₉(t) and OH] | 190–192 | CDCl₃: 1.16(t, J=7.1Hz, 3H), 1.42(s, 18H), 2.42 (s, 3H), 3.34(s, 2H), 4.01(q, J=7.1Hz, 2H), 5.29 (s, 1H), 6.46(d, J=2.2Hz, 1H), 7.05(s, 2H), 7.98 (d, J=2.2Hz, 1H), 8.01(brs, 1H) |
| 17 | CO₂Et | H | Ph | H | —NH—[phenyl with MeO₂C] | 97–100 | DMSO-d₆: 1.17(t, J=7.2Hz, 3H), 3.83(s, 3H), 4.14(q, J=7.2Hz, 2H), 7.16(d, J=8.0Hz, 1H), 7.2–7.3(m, 2H), 7.44(d-d, J=8.0, 8.0Hz, 2H), 7.54(d-d, J=8.0, 8.0Hz, 1H), 7.96(d, J=8.0Hz, 1H), 8.14 (d, J=8.0Hz, 2H), 8.71(s, 1H), 8.82(s, 1H), 11.24 (s, 1H) |
| 18 | CO₂Et | H | Ph | H | —NH—[phenyl with CO₂Me and OH] | 189–191 | DMSO-d₆: 1.14(t, J=7.2Hz, 3H), 3.88(s, 3H), 3.98(q, J=7.2Hz, 2H), 6.99(d, J=8.9Hz, 1H), 7.24 (d-d, J=8.0, 8.0Hz, 1H), 7.4–7.5(m, 3H), 7.67(d, J=3.0Hz, 1H), 8.14(d, J=8.0Hz, 2H), 8.67(s, 1H), 8.72(s, 1H), 10.44(s, 1H), 10.60(brs, 1H) |
| 19 | H | Me | H | Ph | —N—[2-oxopyrrolidinyl] | 156–158 | CDCl₃: 2.33(quintet, J=7.5Hz, 2H), 2.61(s, 3H), 2.69(t, J=7.5Hz, 2H), 4.48(t, J=7.5Hz, 2H), 6.86 (s, 1H), 6.96(s, 1H), 7.4–7.5(m, 3H), 7.9–8.0(m, 2H) |
| 20 | H | Me | H | H | —N—[piperazinyl-N-CHPh₂] | 140–142 | CDCl₃: 2.51(s, 3H), 2.66(t, J=4.9Hz, 4H), 3.72(t, J=4.9Hz, 4H), 4.34(s, 1H), 5.95(s, 1H), 6.43(d, J=2.3Hz, 1H), 7.2–7.5(m, 10H), 7.95(d, J=2.3Hz, 1H) |

TABLE 1-continued

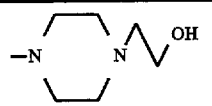

| Ex. No. | R₁ | R₂ | R₃ | R₄ | R₅ | M.p. °C. | ¹H-NMR δ value (internal standard: TMS) |
|---|---|---|---|---|---|---|---|
| 21 | H | Me | H | H | 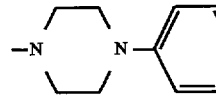 | 57–59 | CDCl₃—CD₃OD: 2.53(s, 3H), 2.67(t, J=5.6Hz, 2H), 2.81(t, J=5.0Hz, 4H), 3.7–3.8(m, 6H), 6.06 (s, 1H), 6.45(d, J=2.3Hz, 1H), 8.01(d, J=2.3Hz, 1H) |
| 22 | H | Me | H | H | 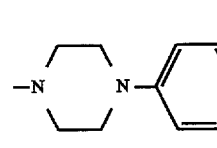 | 199–201 | CDCl₃—CD₃OD: 2.55(s, 3H), 3.41(t, J=5.0Hz, 4H), 3.88(t, J=5.0Hz, 4H), 6.11(s, 1H), 6.47(d, J=2.3Hz, 1H), 6.94(d, J=9.0Hz, 2H), 7.26(d, J=9.0Hz, 2H), 8.04(d, J=2.3Hz, 1H) |
| 23 | H | Me | H | H | 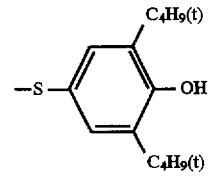 | >223 | CDCl₃—CD₃OD: 2.70(s, 3H), 3.57(t, J=5.1Hz, 4H), 4.5–4.6(br, 4H), 6.52(s, 1H), 6.64(d, J=2.1Hz, 1H), 7.1–7.2(br, 2H), 7.4–7.5(br, 2H), 8.12(d, J=2.1Hz, 1H) |
| 24 | H | Me | H | H | 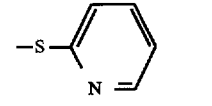 | 194–196 | CDCl₃: 1.48(s, 18H), 2.43(s, 3H), 5.63(s, 1H), 5.92(s, 1H), 6.55(d, J=2.3Hz, 1H), 7.47(s, 2H), 8.14(d, J=2.3Hz, 1H) |
| 25 | H | Me | H | H | 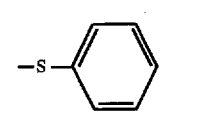 | 170–172 | CDCl₃: 2.50(s, 3H), 6.50(s, 1H), 6.59(d, J=2.3 Hz, 1H), 7.40(d-d-d, J=7.6, 4.8, 1.0Hz, 1H), 7.68(d-t, J=7.6, 1.0Hz, 1H), 7.81(t-d, J=7.6, 1.8Hz, 1H), 8.11(d, J=2.3Hz, 1H), 8.72(d-d-d, J=4.8, 1.8, 1.0Hz, 1H) |
| 26 | H | Me | H | H | —S—Ph | 165–166 | CDCl₃: 2.41(s, 3H), 5.89(s, 1H), 6.56(d, J=2.3Hz, 1H), 7.5–7.7(m, 3H), 7.7–7.8(m, 2H), 8.14(d, J=2.3Hz, 1H) |

EXAMPLE 27

Preparation of 7-(2-carboxyphenyl)amino-5-methylpyrazolo[1,5-a]pyrimidine:

To a solution of 7-(2-methoxycarbonylphenyl)amino-5-methylpyrazolo[1,5-a]pyrimidine (1.0 g) prepared in Example 3 in ethanol (20 ml) is added a 5% sodium hydroxide solution (30 ml), and the mixture is heated with stirring at 100° C. for one hour. After cooling, the mixture is evaporated to remove ethanol, and the residue is neutralized with a 10% hydrochloric acid, and further the pH value of the mixture is adjusted to pH 4 with a saturated aqueous citric acid solution. The precipitated crystal is collected by filtration, and washed with water, ethanol and ethyl ether, and dried to give 7-(2-carboxyphenyl)amino-5-methylpyrazolo[1,5-a]pyrimidine (970 mg) as colorless crystal.

M.p. 261°–262° C. (decomposed)

1H-NMR (DMSO-d₆): δ

2.47 (s, 3H) 6.47 (d, J=1.2 Hz, 1H), 6.76 (s, 1H), 7.27 (t, J=7.6 Hz, 1H), 7.72 (t, J=7.6 Hz, 1H), 7.86 (d, J=7.6 Hz, 1H), 8.07 (d, J=7.6 Hz, 1H), 8.16 (d, J=1.2 Hz, 1H)

EXAMPLES 28 TO 35

The compounds listed in the following Table 2 are obtained in the same manner as in Example 27.

TABLE 2

[Structure: pyrazolo[1,5-a]pyrimidine core with substituents R1, R2, R3, R4, R5]

| Ex. No. | R1 | R2 | R3 | R4 | R5 | M.p. °C. | 1H-NMR δ value (internal standard: TMS) |
|---|---|---|---|---|---|---|---|
| 28 | H | Me | H | H | —NH—(phenyl: OH, CO2H) | 284–285 (dec.) | CDCl3—CD3OD: 2.48(s, 3H), 6.00(s, 1H), 6.46(d, J=1.8Hz, 1H), 7.10(d, J=9.2Hz, 1H), 7.32(d-d, J=9.2, 2.7Hz, 1H), 7.92(d, J=2.7Hz, 1H), 8.06(d, J=1.8Hz, 1H) |
| 29 | H | Me | H | Ph | —NH—(phenyl: OH, CO2H) | 310–312 (dec.) | DMSO-d6: 2.45(s, 3H), 6.12(s, 1H), 6.99(s, 1H), 7.13(d, J=8.7Hz, 1H), 7.4–7.6(m, 3H), 7.64(d-d, J=8.7, 2.6Hz, 1H), 7.87(d, J=2.6Hz, 1H), 8.16(d, J=7.9Hz, 2H) |
| 30 | H | Me | Ph | H | —NH—(phenyl: OH, CO2H) | 289–290 (dec.) | DMSO-d6: 2.43(s, 3H), 6.03(s, 1H), 7.08(d, J=8.8Hz, 1H), 7.20(dd, J=8.0, 8.0Hz, 1H), 7.40(d-d, J=8.0, 8.0Hz, 1H), 7.60(d-d, J=8.8, 2.6Hz, 1H), 7.82(d, J=2.6Hz, 1H), 8.18(d, J=8.0Hz, 2H), 8.66(s, 1H), 9.84(s, 1H) |
| 31 | H | Me | Ph | H | —NH—(phenyl: NaO2C) | >300 | DMSO-d6: 2.53(s, 3H), 6.79(s, 1H), 7.06(t, J=7.2Hz, 1H), 7.18(t, J=7.2Hz, 1H), 7.4–7.5(m, 3H), 7.66(d, J=8.3Hz, 1H), 8.05(d, J=6.2Hz, 1H), 8.85(d, J=8.3Hz, 2H), 8.60(s, 1H), 14.42(s, 1H) |
| 32 | H | Me | CO2H | H | —NH—(phenyl: C4H9(t), OH, C4H9(t)) | 240–241 (dec.) | DMSO-d6: 1.41(s, 18H), 2.42(s, 3H), 6.22(s, 1H), 7.17(s, 2H), 7.15(s, 1H), 8.47(s, 1H), 9.84(s, 1H) |
| 33 | H | Me | CO2H | H | —NH—(phenyl: OH, CO2H) | 227–228 | DMSO-d6: 2.40(s, 3H), 6.12(s, 1H), 7.04(d, J=8.7Hz, 1H), 7.53(d-d, J=8.7, 2.7Hz, 1H), 7.76(d, J=2.7Hz, 1H), 8.47(s, 1H), 10.00(brs, 1H) |
| 34 | CO2H | H | Ph | H | —NH—(phenyl: OH, CO2H) | 254–255 (dec.) | DMSO-d6: 6.89(d, J=8.9Hz, 1H), 7.25(d-d, J=8.0, 8.0Hz, 1H), 7.3–7.5(m, 3H), 7.64(d, J=2.7Hz, 1H), 8.12(d, J=8.0Hz, 2H), 8.61(s, 1H), 8.76(s, 1H), 10.99(s, 1H) |
| 35 | CH2CO2H | Me | H | H | —NH—(phenyl: C4H9(t), OH, C4H9(t)) | 252–254 (dec.) | DMSO-d6: 1.35(s, 18H), 2.32(s, 3H), 3.25(s, 2H), 6.39(d, J=2.2Hz, 1H), 6.87(s, 2H), 6.99(s, 1H), 8.04(d, J=2.2Hz, 1H), 8.95(s, 1H) |

EXAMPLE 36

Preparation of 7-(3,5-di-t-butyl-4-hydroxyphenyl)-amino-3-hydroxymethyl-5-methylpyrazolo[1,5-a]pyrimidine:

To a suspension of LiAlH₄ (840 mg) in anhydrous ether (50 ml) is added dropwise a solution of 7-(3,5-di-t-butyl-4-hydroxyphenyl)amino-3-ethoxycarbonyl-5-methyl-pyrazolo[1,5-a]pyrimidine (3.5 g) prepared in Example 10 in dry THF (50 ml) with ice-cooling, and the mixture is stirred at the same temperature for 30 minutes, and further stirred at room temperature for one hour. To the mixture are added ethyl acetate and water to decompose excess LiAlH₄, and the mixture is filtered with celite. The filtrate is diluted with ethyl acetate, and washed with a saturated aqueous $Na_2S_2O_4$ solution and a saturated sodium chloride solution, and dried over anhydrous magnesium sulfate. The mixture is evaporated to remove the solvent, and the residue is purified by silica gel column chromatography (solvent; ethyl acetate/dichloroethane=2:1→chloroform/methanol=8:1). The obtained crystal is washed with ethyl ether to give 7-(3,5-di-t-butyl-4-hydroxyphenyl)amino-3-hydroxymethyl-5-methylpyrazolo[1,5-a]pyrimidine (2.3 g) as colorless crystal.

M.p. 194°–196° C.

$^1$H-NMR (DMSO-$d_6$): δ

1.41 (s, 18H), 2.36 (s, 3H), 4.60 (d, J=5.2 Hz, 2H), 4.79 (t, J=5.2 Hz, 1H), 6.04 (s, 1H), 7.10 (brs, 1H), 7.17 (s, 2H), 8.06 (s, 1H), 9.44 (brs, 1H)

EXAMPLE 37

Preparation of 6,7-dihydro-8-(3,5-di-t-butyl-4-hydroxyphenyl)amino-5H-cyclopenta[d]pyrazolo[1,5-a]-pyrimidine:

Ethyl 2-oxocyclopentanecarboxylate (31 g) and 3-aminopyrazole (17.4 g) are dissolved in acetic acid (300 ml), and the mixture is heated at 100° C. for 3 hours. After allowed to stand for cooling, the resulting crystal is collected by filtration, and washed successively with water and diethyl ether, and further recrystallized from dichloromethane-diethyl ether to give a crystal (22.3 g) having a melting point of more than 280° C.

Subsequently, the crystal obtained above (9 g) and N,N-diethylaniline (15 ml) are added to phosphorus oxychloride (90 ml), and the mixture is heated at 80° C. for three hours. After the reaction is complete, the mixture is concentrated under reduced pressure, and the residue is poured into ice-water, and extracted with dichloromethane. The organic layer is washed with a saturated sodium chloride solution. The residue is dried over anhydrous sodium sulfate, and evaporated to remove the solvent. The residue is crystallized from n-hexane to give a crystal (9.9 g).

The above crystal (3.9 g), 3,5-di-t-butyl-4-hydroxyaniline hydrochloride (5.2 g) and N,N-diethylaniline (5 ml) are added to toluene (60 ml), and the mixture is heated at 100° C. for three hours. The mixture is treated in the same manner as in Example 1, and the resulting crude product is purified by silica gel column chromatography (solvent; dichloromethane→dichloromethane/methanol=50:1), and further recrystallized from dichloromethane/diethyl ether to give the desired compound (3.8 g).

M.p. 255°–257° C. (decomposed)

$^1$H-NMR (CDCl$_3$): δ

1.45 (s, 18H), 1.96 (quintet, J=7.3 Hz, 2H), 2.22 (t, J=7.3 Hz, 2H), 2.89 (t, J=7.3 Hz, 2H), 5.30 (s, 1H), 6.40 (d, J=2.3 Hz, 1H), 7.07 (s, 2H), 7.97 (d, J=2.3 Hz, 1H), 7.97 (brs, 1H)

EXAMPLE 38–48

The compounds listed in the following Table 3 are obtained in the same manner as in Example 37.

TABLE 3

| Ex. No. | $R_1$ | $R_2$ | $R_3$ | $R_4$ | $R_5$ | M.p. °C. | $^1$H-NMR δ value (internal standard: TMS) |
|---|---|---|---|---|---|---|---|
| 38 | H | —(CH$_2$)$_3$CH$_3$ | H | H | —NH—C$_6$H$_2$(C$_4$H$_9$(t))$_2$—OH | 200–202 | CDCl$_3$: 0.93(t, J=7.3Hz, 3H), 1.3–1.5(m, 2H), 1.47 (s, 18H), 1.6–1.8(m, 2H), 2.69(t, J=7.8Hz, 2H), 5.28(s, 1H), 6.10(s, 1H), 6.46(d, J=2.3Hz, 1H), 7.17 (s, 2H), 7.85(brs, 1H), 8.01(d, J=2.3Hz, 1H) |
| 39 | H | —(CH$_2$)$_3$CH$_3$ | H | H | —S—C$_6$H$_2$(C$_4$H$_9$(t))$_2$—OH | 155–157 | CDCl$_3$: 0.88(t, J=7.3Hz, 3H), 1.2–1.4(m, 2H), 1.47 (s, 18H), 1.5–1.7(m, 2H), 2.65(t, J=7.6Hz, 2H), 5.63(s, 1H), 5.92(s, 1H), 6.57(d, J=2.4Hz, 1H), 7.48 (s, 2H), 8.14(d, J=2.4Hz, 1H) |
| 40 | H | Ph | H | H | —NH—C$_6$H$_2$(C$_4$H$_9$(t))$_2$—OH | 212–214 | CDCl$_3$: 1.48(s, 18H), 5.31(s, 1H), 6.61(d, J=2.2Hz, 1H), 6.65(s, 1H), 7.24(s, 2H), 7.4–7.5(m, 3H), 7.9–8.0(m, 3H), 8.07(d, J=2.2Hz, 1H) |

TABLE 3-continued

| Ex. No. | R₁ | R₂ | R₃ | R₄ | R₅ | M.p. °C. | ¹H-NMR δ value (internal standard: TMS) |
|---|---|---|---|---|---|---|---|
| 41 | H | Ph | H | H | -S-C₆H₂(C₄H₉(t))₂-OH | 229–231 | CDCl₃: 1.49(s, 18H), 5.65(s, 1H), 6.55(s, 1H), 6.72 (d, J=2.4Hz, 1H), 7.4–7.5(m, 3H), 7.55(s, 2H), 7.7–7.8(m, 2H), 8.21(d, J=2.4Hz, 1H) |
| 42 | H | -CH(CH₃)₂ | H | H | -NH-C₆H₂(C₄H₉(t))₂-OH | 220–224 (dec.) | CDCl₃: 1.30(d, J=6.9Hz, 6H), 1.47(s, 18H), 2.97 (septet, J=6.9Hz, 1H), 5.27(s, 1H), 6.18(s, 1H), 6.48 (d, J=2.3Hz, 1H), 7.19(s, 2H), 7.88(brs, 1H), 8.01 (d, J=2.3Hz, 1H) |
| 43 | H | -CH(CH₃)₂ | H | H | -S-C₆H₂(C₄H₉(t))₂-OH | 185–187 | CDCl₃: 1.17(d, J=6.9Hz, 6H), 1.47(s, 18H), 2.91 (septet, J=6.9Hz, 1H), 5.62(s, 1H), 5.92(s, 1H), 6.58 (d, J=2.3Hz, 1H), 7.48(s, 2H), 8.14(d, J=2.3Hz, 1H) |
| 44 | H | Et | H | H | -NH-C₆H₂(C₄H₉(t))₂-OH | 230–232 | CDCl₃: 1.30(t, J=7.6Hz, 3H), 1.47(s, 18H), 2.73(q, J=7.6Hz, 2H), 5.28(s, 1H), 6.12(s, 1H), 6.46(d, J=2.3Hz, 1H), 7.18(s, 2H), 7.87(brs, 1H), 8.01(d, J=2.3Hz, 1H) |
| 45 | H | Et | H | H | -S-C₆H₂(C₄H₉(t))₂-OH | 213–214 | CDCl₃: 1.20(t, J=7.6Hz, 3H), 1.47(s, 18H), 2.69(q, J=7.6Hz, 2H), 5.62(s, 1H), 5.94(s, 1H), 6.57(d, J=2.3Hz, 1H), 7.48(s, 2H), 8.14(d, J=2.3Hz, 1H) |
| 46 | H | cyclopropyl | H | H | -NH-C₆H₂(C₄H₉(t))₂-OH | 221–223 | CDCl₃: 0.9–1.1(m, 4H), 1.47(s, 18H), 1.9–2.0(m, 1H), 5.29(s, 1H), 6.03(s, 1H), 6.38(d, J=2.1Hz, 1H), 7.17(s, 2H), 7.83(brs, 1H), 7.97(d, J=2.1Hz, 1H) |
| 47 | H | cyclopropyl | H | H | -S-C₆H₂(C₄H₉(t))₂-OH | 206–207 | CDCl₃: 0.9–1.0(m, 4H), 1.49(s, 18H), 1.85(quintet, J=6.5Hz, 1H), 5.62(s, 1H), 5.84(s, 1H), 6.48(d, J=2.3Hz, 1H), 7.48(s, 2H), 8.10(d, J=2.3Hz, 1H) |

TABLE 3-continued

| Ex. No. | R₁ | R₂ | R₃ | R₄ | R₅ | M.p. °C. | ¹H-NMR δ value (internal standard: TMS) |
|---|---|---|---|---|---|---|---|
| 48 | —CH₂—CH₂—CH₂— | | | H | H | 209–210 (dec.) | CDCl₃: 1.44(s, 18H), 1.91(quintent, J=7.4Hz, 2H), 2.07(t, J=7.4Hz, 2H), 2.87(t, J=7.4Hz, 2H), 5.54 (s, 1H), 6.53(d, J=2.3Hz, 1H), 7.49(s, 2H), 8.09(d, J=2.3Hz, 1H) |

(R₃ = S-phenyl with 2,6-di-C₄H₉(t) and 4-OH)

Pharmacological Experiment 1

Cyclooxygenase inhibitory activity test 1:

The preparation of sheep seminal vesicle microsome, which is a crude enzyme solution, and the analysis of the cyclooxygenase activity were carried out according to the method of Miyamoto et al. as follows [cf. Proc. Natl. Acad. Sci., U.S.A., 71, 3645 (1974) and J. Biol. Chem., 251, 2629 (1976)].

That is, a test compound was added to a microsome solution, and the mixture was incubated at 24° C. for two minutes, and then, thereto was added a substrate, $^{14}C$-arachidonic acid. The mixture was further incubated for two minutes, and the reaction was quenched with a mixture of ether/methanol/0.2M citric acid (30:4:1), and extracted to collect a product produced by cyclooxygenase. The extract was spotted on a thin layer plate and the plate was developed. The fractions containing the arachidonic acid, prostaglandin $E_2$ ($PGE_2$) and the other parts were collected by scratching, respectively. Each part was measured with a scintillation counter, by which the cyclooxygenase activity therein was estimated.

The compounds prepared in Examples 2, 38, 44 and 46 were tested in the above experiment, and there were obtained the concentrations of the test compounds required to reduce the cyclooxygenase activity to 50% (cyclooxygenase inhibitory rate; $IC_{50}$ value).

As a result, the $IC_{50}$ value of the compound prepared in Example 2 was $3\times10^{-7}M$, which was 27.8 times as high as that of indomethacin which was used as a reference compound. That means that the present compound has extremely excellent inhibitory activity.

Pharmacological Experiment 2

Cyclooxygenase inhibitory activity test 2:

Using as a standard the $IC_{50}$ value of the compound prepared in Example 2 (i.e. $3\times10^{-7}M$) obtained in the above pharmacological experiment 1, each test compound (the present compounds and indomethacin as a reference compound) was tested by the same experiment in the same concentration (fixed), and the cyclooxygenase activity was measured, which was compared with that of the control group ($PGE_2$ producing rate) and expressed as inhibitory rate (%).

The results are shown in the following Table 4.

TABLE 4

| Test compound | Inhibitory rate (%) |
|---|---|
| Compound of Ex. 2 | 65.0 |
| Compound of Ex. 38 | 48.2 |
| Compound of Ex. 44 | 55.9 |
| Compound of Ex. 46 | 50.5 |
| Indomethacin (reference compound) | 12.4 |

As shown in Table 4, all the present compounds tested have extremely excellent cyclooxygenase inhibitory activity as compared with indomethacin, from which it is apparent that the present compounds are very useful as an anti-inflammatory agent.

Preparation 1: Preparation of Ointment

Using the compound of Example 2 (2 g), liquid paraffin (5 g), bees wax (5 g), crotamiton (5 g), self-emulsifiable-type glyceryl monostearate (3 g) and white soft paraffin (80 g) (totally, 100 g) as components, the compound of Example 2 is suspended in the above components with warming to give a uniform suspension, which is further rapidly cooled to give an anti-inflammatory agent of the present invention in the form of ointment.

Preparation 2: Preparation of Ointment

Using the compound of Example 2 (2 g), glyceryl monostearate (20 g), self-emulsifiable-type glyceryl monostearate (3 g), crotamiton (5 g) and medium-chain fatty acid triglyceride (70 g) (totally, 100 g) as components, the compound of Example 2 is suspended in the above components with warming to give a uniform suspension, which is further rapidly cooled to give an anti-inflammatory agent of the present invention in the form of ointment.

Preparation 3: Preparation of Cream

The compound of Example 2 (2 g) is suspended with warming in a mixture of glyceryl monostearate (20 g), cetostearyl alcohol (2 g), octyldodecanol (10 g), crotamiton (10 g), polyoxyethylene sorbitan monooleate (3.3 g), sorbitan monooleate (1.2 g) and butyl paraben (0.01 g) to give a uniform suspension. Separately, conc. glycerin (5 g) and methyl paraben (0.02 g) are dissolved in purified water (totally, 100 g) with warming, and this solution is added with stirring to the above suspension, and subjected to emulsification with rapid-stirring, and cooled to give an anti-inflammatory agent of the present invention in the form of cream.

We claim:

1. A pyrazolo [1,5-a]pyrimidine derivative of the general formula:

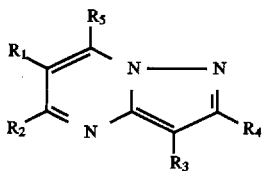

wherein $R_1$, $R_2$, $R_3$ and $R_4$ are the same or different and are each a hydrogen atom, a phenyl group, a lower alkyl group which may optionally be substituted by a hydroxyl group, or a cycloalkyl group, or $R_1$ and $R_2$ may combine with each other to form a lower alkylene group; $R_5$ is a group of the formula: —$SR_6$ or a group of the formula: —$NR_7R_8$ in which $R_6$ is a pyridyl group or a phenyl group which may optionally be substituted by 1 to 3 groups selected from a hydroxyl group and a lower alkyl group; and $R_7$ and $R_8$ are a hydrogen atom or a phenyl group which may optionally be substituted by 1 to 3 groups selected from a hydroxyl group, a lower alkyl group, a lower alkoxycarbonyl group and carboxyl group, provided that $R_7$ and $R_8$ are not simultaneously hydrogen atoms, or $R_7$ and $R_8$ may combine with each other to form with a nitrogen atom with which they bond 1-pyrrolidinyl group, 2-oxo-1-pyrrolidinyl group, or 1-piperazinyl group substituted by a member selected from the group consisting of a phenyl group having optionally a halogen- or trihalomethyl-substituent, a hydroxy-lower alkyl group or a diphenyl-lower alkyl group, or a salt thereof.

2. The compound according to claim 1, wherein $R_1$, $R_2$, $R_3$ and $R_4$ are the same or different and are each a hydrogen atom, a phenyl group, a lower alkyl group or a cycloalkyl group; $R_5$ is a group of the formula: —$SR_6$ or a group of the formula: —$NR_7R_8$ in which $R_6$ is a phenyl group which may optionally be substituted by 1 to 3 groups selected from hydroxyl group and a lower alkyl group; and $R_7$ and $R_8$ are hydrogen atom or a phenyl group which may optionally be substituted by 1 to 3 groups selected from hydroxyl group, a lower alkyl group and carboxyl group, provided that $R_7$ and $R_8$ are not simultaneously hydrogen atom.

3. 5-Methyl-7-(3,5-di-t-butyl-4-hydroxyphenyl)aminopyrazolo[1,5-a]pyrimidine.

* * * * *